(12) United States Patent
Nakao

(10) Patent No.: US 7,744,895 B2
(45) Date of Patent: Jun. 29, 2010

(54) METHODS OF TREATING ALLERGIES USING TGF-β1 AND ALLERGENS

(75) Inventor: Atsuhito Nakao, Yamanashi (JP)

(73) Assignee: Yamanashi University, Kofu-shi (JP)

( * ) Notice: Subject to any disclaimer, the term of this patent is extended or adjusted under 35 U.S.C. 154(b) by 0 days.

(21) Appl. No.: 11/363,371

(22) Filed: Feb. 28, 2006

(65) Prior Publication Data

US 2007/0048328 A1    Mar. 1, 2007

(30) Foreign Application Priority Data

Aug. 31, 2005    (JP) .............................. 2005-252912

(51) Int. Cl.
- *A61K 39/00*    (2006.01)
- *A61K 38/00*    (2006.01)
- *A61K 47/00*    (2006.01)

(52) U.S. Cl. ...................... 424/185.1; 514/12; 424/439

(58) Field of Classification Search .................. None
See application file for complete search history.

(56) References Cited

U.S. PATENT DOCUMENTS 5,451,411 A    9/1995    Gombotz et al.
5,461,033 A *  10/1995   Donnet et al. ................. 514/12

FOREIGN PATENT DOCUMENTS

EP    0527283 B1    2/1993

OTHER PUBLICATIONS

Laiho et al., Pediatr Res. Apr. 2003;53(4):642-7. Epub Jan. 29, 2003.*
Janeway et al., Eds. Immunobiology: The Immune System Health and Disease. 5th Ed. Garland Publishing. New York. 2001, pp. 471-490.*
Saito et al., Clin Exp Immunol. Oct. 1993;94(1):220-224, Abstract Only.*
Ohtsuka et al., Curr Opin Gastroenterol. Nov. 2000;16(6):541-545.*
Holt. Allergy. 1993;53(Suppl 46):16-19.*
Okamoto et al., International Immunology. Apr. 18, 2005; 17(6):705-712.*
Kalliomaki et al., J Allergy Clin Immunol. Dec. 1999; 104(6):1251-7.*
Kulkami et al., PNAS USA. Jan. 15, 1993; 90(2):770-774.*
Mersmann, Prog Food Nutr Sci., 1987 11(2):175-201.*
Zemann et al., Allergy Clin Immunol. May 2003;111(5):1069-75.*

(Continued)

*Primary Examiner*—Cherie M Woodward
(74) *Attorney, Agent, or Firm*—Birch, Stewart, Kolasch & Birch, LLP

(57) ABSTRACT

The invention provides an allergy prevention method or treatment method, diets and oral drugs enabling prevention/treatment of allergic symptoms without trouble such as systemic adverse reaction, immune deficiency and the like caused by transdermal/intravenous administration of TGF-β. The allergy prevention method or treatment method is to orally administer 100 μg/kg or more of transforming growth factor-beta (TGF-β) relative to a weight of an administration target body and thereby selectively suppress Th2 immune response, while with respect to the diets and oral drugs, the content is set to contain an effective amount of transforming growth factor-beta (TGF-β) therein.

18 Claims, 4 Drawing Sheets

OTHER PUBLICATIONS

Oddy et al. ("J Allergy Clin Immunol. Oct. 2003;112(4):723-8).*

Oddy et al., (Pediatr Allergy Immunol. Jul. 9, 2009. pp. 1-13) [Epub ahead of print].*

Meade et al., "Transforming Growth Factorβ₁ Inhibits Murine Immediate and Delayed Type Hypersensitivity" J immunology, vol. 149, 1992, pp. 521-528.

I. Penttila, "Effects of Transforming Growth Factor-Beta and Formula Feeding on Systemic Immune Responses to Dietary β-Lactoglobulin in Allergy-Prone Rats," Pediatric Research, vol. 59, No. 5, 2006, pp. 650-655.

Coerper et al., "Recombinant Human Transforming Growth Factor Beta 3 Accelerates Gastric Ulcer Healing in Rats," Scand J. Gastroenterol, vol. 32, 1997, pp. 985-990.

Hirshberg et al., "TGF-β3 in the Treatment of Pressure Ulcers: A Preliminary Report," Advances in Skin & Wound Care, vol. 41, Mar./Apr. 2001, pp. 91-95.

Hawkes et al., "Variations in Transforming Growth Factor Beta in Human Milk are not Related to Levels in Plasma," Cytokine, vol. 17, No. 4, Feb. 2002, pp. 182-186.

Derynck et al., "The Murine Transforming Growth Factor-β Precursor," The Journal of Biological Chemistry, vol. 261, No. 10, Apr. 1986, pp. 4377-4379.

J. Massague, "The Transforming Growth Factor-β Family," Annu. Rev. Cell Biol., vol. 6, 1990, pp. 597-641.

A. K. Abbas & A. H. Lichtman, *Cellular and Molecular Immunology*, Fifth Edition, 2003, Elsevier Science (USA), Ch. 19, pp. 432-435.

Okamoto et al., International Immunology vol. 17, No. 6, pp. 705-712, Jun. 2005; Epub Apr. 18, 2005.

Oddy, PhD et al., "TGF-B in human milk is associated with wheeze in infancy" J. Allergy and Clinical Immunology vol. 112, pp. 723-728 (Oct. 2003).

Saito et al., Clin Exp Immunol, "Transforming growth factor-beta (TGF-B) in human milk" vol. 94, pp. 220-224(1993).

Y. Chen et al, "Induction of oral tolerance to myelin basic protein in CD8-depleted mice: both CD4+ and CD8+ cells mediate active suppression", J. Immunology, 1995, vol. 155, pp. 910-916.

J.J. Letterio, et al, "Regulation of Immune Responses by TGF-β", Annu. Rev. Immunol., 1998, vol. 16, pp. 137-161.

Office Action dated Sep. 21, 2009 which issued in related Canadian Application No. 2,538,408.

* cited by examiner

1. OVA
2. OVA + TGF-β + Control Ab
3. OVA + TGF-β + αTGF-β Ab

1. OVA
2. OVA + TGF-β + Control Ab
3. OVA + TGF-β + αTGF-β Ab

METHODS OF TREATING ALLERGIES USING TGF-β1 AND ALLERGENS

BACKGROUND OF THE INVENTION

1. Field of the Invention

The present invention relates to an allergy prevention method or treatment method, diet and oral drug, and more particularly, to an allergy prevention method or treatment method, diet and oral drug that modify immune response different from that of transdermal/intravenous administration by oral administration.

2. Description of the Related Art

Transforming growth factor-β (TGF-β) is one of bioactive cytokines, identified during the 1980s, contained abundantly in human milk, and a multifunctional cytokine that regulates cell growth, survival and differentiation, which is disclosed in "Transforming growth factor-beta (TGF-β) in human milk", Clin Exp Immunol Vol. 94 (1): 220-224, 1993 Oct.

TGF-β is considered an essential molecule in survival of living being, because the gene arrangement is conserved with excellence in fly, frog, mouse, human and the like, a TGF-β receptor exits in almost all the cells in the body, and mice with artificially lacked TGF-β (gene knockout mice) die during a fetal period.

From previous epidemiological studies, it is reported that an amount of TGF-β taken from human milk is inversely proportional to a rate of crisis of allergic diseases such as atopic dermatitis during infancy (see "TGF-β in human milk is associated with wheeze in infancy", J Allergy Clin Immunol Vol. 112 (4): 723-728, 2003 Oct.), and that the rate of crisis of allergic diseases of infants decreases when mothers take probiotics during pregnant and lactation, where the result is associated with the amount of TGF-β in human milk.

Further, for the purpose of prevention and treatment of diseases, studies of TGF-β transdermal/intravenous administration have been performed on various zoonoses mice. There are also examples that clinical tests are actually performed for the purpose of prevention and treatment of human diseases.

However, disease prevention/treatment effects of TGF-β transdermal/intravenous administration have not been determined, and there remain many issues to overcome by practical use as a drug, such as weakness of the action to diseases, systemic adverse reaction provoked by administration of TGF-β and the like.

Allergic diseases such as pollinosis, bronchial asthma, atopic dermatitis, allergic asthma and the like grow year after year, and are becoming a social issue.

In recent years, the food allergy has also surged mainly among infants. They develop eczema and/or hives by intake of an allergy causal substance contained in a diet, and in the serious case, may die by anaphylactic shock. Causal substances of the food allergy depend on individuals, but are usually familiar foods such as milk, egg, wheat, rice, buckwheat noodle, seafood and the like. It is difficult to manage to live while completely keeping away from the allergy causal substances in modern society.

The inventor of the present invention noted the report (see "TGF-β in human milk is associated with wheeze in infancy", J Allergy Clin Immunol Vol. 112 (4): 723-728, 2003 Oct.) that the intake of TGF-β from human milk is inversely proportional to the number of crises of asthma of infants, and proceeded with empirical researches to prevent and/or treat food allergic diseases by oral administration of TGF-β.

It has conventionally been considered that orally taken protein molecules are decomposed in gastrointestine and do not exert the action systemically, and sufficient verification has not been performed also on TGF-β. The inventor of the invention found that as a result of verification of effects of TGF-β oral administration on the immune system using model animals, when high-dose TGF-β is orally administered, TGF-β is not decomposed, and modifies immune response in a manner specific to oral administration different from that in conventional transdermal/intravenous administration.

In the case of conventional transdermal/intravenous administration, while Th2 immune response (production of IgE antibody and the like) involved in the allergy reaction is suppressed, Th1 immune response to the cancer and infection (cell immunity such as the defense reaction to cancer cells and pathogens) is also suppressed. The immune response is thus totally suppressed by administration of TGF-β, and there is the risk of immune deficiency.

The inventor verified the effects exerted on the systemic immune system by orally administering TGF-β to food allergy model mice. In the stage prior to verification, it was expected that TGF-β, protein molecule, is decomposed in gastrointestine, and does not exhibit the immune suppression effect as in transdermal/intravenous administration. However, actually, orally administered TGF-β selectively suppressed only Th2 immune response involved in the allergic reaction, while enhancing Th1 immune response to the cancer and infection, and thus exhibited the immune suppression effect different from that in transdermal/intravenous administration. Therefore, the inventor found that TGF-β is a protein molecule, but when orally administered, is not decomposed in gastrointestine, and that orally administered TGF-β modifies specific immune response, and reached completion of the invention.

BRIEF SUMMARY OF THE INVENTION

It is an object of the invention to provide an allergy prevention method or treatment method, diets and oral drugs enabling prevention/treatment of allergic symptoms without trouble such as systemic adverse reaction, immune deficiency and the like caused by transdermal/intravenous administration of TGF-β.

In other words, it is a feature of the allergy prevention method or treatment method of the invention selectively suppressing Th2 immune response by orally administering 100 μg/kg or more of transforming growth factor-beta (TGF-β) relative to a weight of an administration target body.

According to this method, Th2 immune response is selectively suppressed, and it is thereby possible to prevent crises of allergic symptoms, and alleviate or treat already developed allergic symptoms.

Further, in the method of suppressing Th2 immune response, while maintaining or enhancing Th1 immune response, as well as prevention or treatment of allergy, such a method can be used in prevention and treatment of various diseases such as cancers and infections.

Furthermore, it is another feature of the allergy prevention method or treatment method of the invention orally administering TGF-β simultaneously with intake of a causal substance of a food allergy. According to this method, it is possible to prevent crises of allergic symptoms such as eczema, hives, anaphylactic shock and the like caused by intake of the causal substance of a food allergy.

A diet of the invention is selected from a group consisting of foods, health foods, functional foods, dietary supplements, foods for specified health use and quasi drugs characterized by selectively suppressing Th2 immune response by containing a predetermined amount of transforming growth factor-beta (TGF-β). By this means, high-dose TGF-β is orally taken by intake of the food, Th2 immune response is selectively suppressed, and it is thereby possible to prevent and alleviate allergic symptoms.

Further, in diets characterized by suppressing Th2 immune response while maintaining or enhancing Th1 immune response, as well as the effect of preventing and alleviating the allergy, it is possible to exert effects of preventing various diseases such as cancers and infections, maintaining health, and the like.

Furthermore, it is a feature of the diets of the invention that a predetermined amount of transforming growth factor-beta (TGF-β) is added to foods and the like each containing a causal substance of a food allergy.

An oral drug of the invention is selected from a group consisting of allergy preventive drugs, allergy treatment drugs, immune activation drugs, antitumor drugs, antiinfectants, and antiviral drugs characterized by selectively suppressing Th2 immune response by containing a predetermined amount of transforming growth factor-beta (TGF-β). By this means, orally administered high-dose TGF-β suppresses Th2 immune response, and can thus be used in preventing and/or treating allergic symptoms.

Further, in oral drugs characterized by selectively suppressing Th2 immune response while maintaining or enhancing Th1 immune response, as well as the effect of preventing and alleviating the allergy, it is possible to use in preventing and/or treating symptoms of various diseases such as cancers and infections, and the like.

Furthermore, an oral drug of the invention is selected from a group consisting of immune activation drugs, antitumor drugs, antiinfectants, and antiviral drugs characterized by enhancing Th1 immune response by containing a predetermined amount of transforming growth factor-beta (TGF-β). By this means, since the immunity is enhanced by administration of TGF-β, it is possible to use in preventing and/or treating symptoms of various diseases such as cancers and infections, and the like.

According to the invention, by orally administering high-dose TGF-β, it is possible to prevent or treat allergic diseases without trouble such as adverse reaction, immune deficiency and the like developing in transdermally/intravenously administrating TGF-β. Further, by taking TGF-β simultaneously with an allergy causal substance, it Is possible to prevent crises of food allergic symptoms.

Furthermore, such administration is used in diets having effects of preventing allergic symptoms and various diseases such as cancers and infections and/or maintaining health, and in oral drugs used in preventing or treating allergic symptoms and various diseases.

BRIEF DESCRIPTION OF THE DRAWINGS

The above and other objects and features of the invention will appear more fully hereinafter from a consideration of the following description taken in connection with the accompanying drawing wherein one example is illustrated by way of example, in which.

DETAILED DESCRIPTION OF THE INVENTION

Figure 1A:
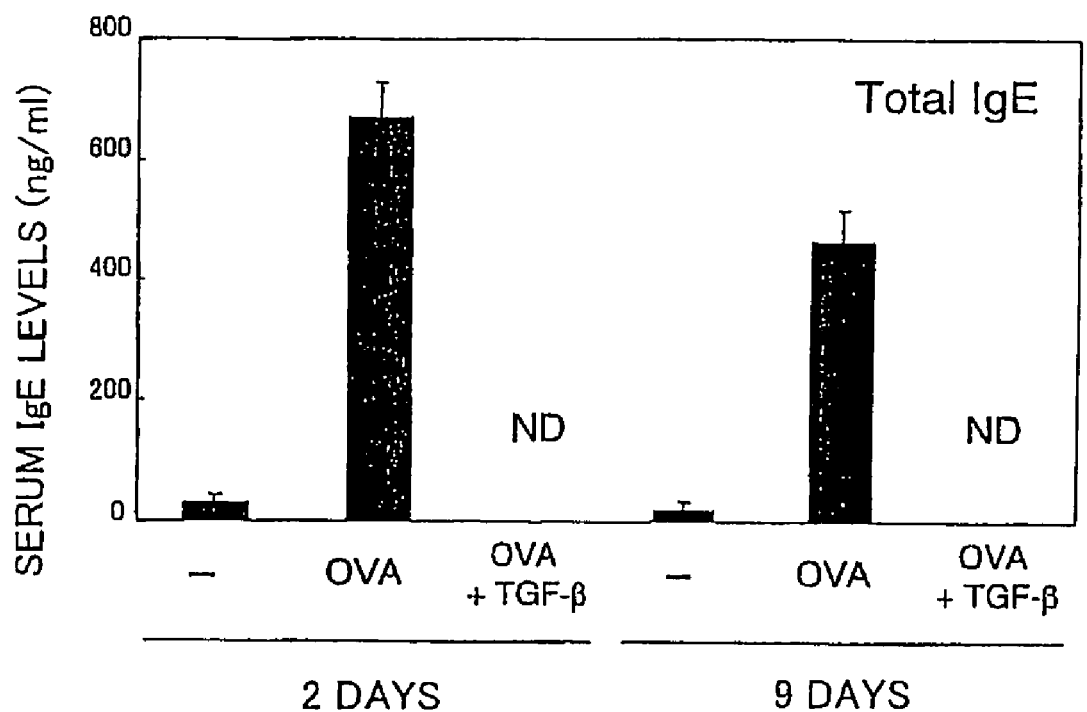
FIG. 1A is a graph illustrating suppression of production of serum IgE antibody by orally administered TGF-β of Embodiment 1.

The invention is of an allergy prevention method or treatment method of selectively suppressing Th2 immune response by orally administering 100 µg/kg or more of transforming growth factor-beta (TGF-β) relative to a weight of an administration target body. Further, the invention is of an allergy prevention method or treatment method characterized by suppressing Th2 immune response while maintaining or enhancing Th1 immune response by orally administering the TGF-β.

The oral administration amount of 100 µg/kg or more of the TGF-β indicates an intake or TGF-β per day, and was calculated based on experimental data of the inventor of the invention and so on.

An administration amount of TGF-β useful as the allergy prevention method or treatment method is preferably set at a range of 100 µg/kg to 250 µg/kg relative to a weight of an administration target body, and more preferably, at a range of 150 µg/kg to 250 µg/kg relative to a weight of an administration target body.

It is considered that since TGF-β is abundantly contained in human milk and taken during infancy to grow the infant, the human has a pathway to metabolize orally taken TGF-β. TGF-β can thus be considered safe in oral administration within the range of an intake such that the human takes TGF-β from human milk during infancy.

Further, TGF-β has high preservation stability among different species, and it is confirmed in conventional studies that TGF-β reacts mutually between different species. It is therefore considered that oral administration of TGF-β of foreign origin has the same effect as that of TGF-β of human origin. However, in terms of safety, it is preferable that TGF-β used in allergy suppression and/or treatment drugs, medical components, and diets of the invention is TGF-β of human origin.

Although there are significant differences depending on bodies and seasons to take human milk, an amount of TGF-β contained in human milk ranges from 500 ng/ml to 1500 µg/ml, and a maximum intake of TGF-β relative to the weight is 200 µg/kg calculated from a weight of an infant to take the milk, a milk intake per day and the like. It is thus estimated that approximately maximum 200 µg/kg of TGF-β can be orally administered safely to the human relative to a weight of an administration target body.

It is a feature of the allergy prevention method and treatment method of the invention orally administering TGF-β simultaneously with intake of a causal substance of a food allergy. However, provided that TGF-β is passed through digestive-system organs such as gastrointestine substantially simultaneously with the causal substance, TGF-β may be administered before or after intake of the causal substance.

Further, it is considered that the human is not only a target for the allergy prevention method or treatment method of the invention, and that the invention is applicable to mammals whose milk contains TGF-β.

The invention is of a diet selected from a group consisting of foods, health foods, functional foods, dietary supplements, foods for specified health use and quasi drugs characterized by selectively suppressing Th2 immune response by containing a predetermined amount of transforming growth factor-beta (TGF-β). Further, the invention is of a diet characterized by suppressing Th2 immune response while maintaining or enhancing Th1 immune response by oral administration of the TGF-β. Furthermore, the invention is of a diet characterized by enhancing Th1 immune response by oral administration of the TGF-β.

Specific examples of the diet include dairy products such as artificial milk and ready-made food for infants, daily products such as yoghurt, milk beverages and the like, confectioneries, noodle and grains, convenience foods, supplements and the like.

Among diets containing a food allergy causal substance are beverages such as milk, yoghurt and the like, confectionaries such as chocolate, biscuit, pudding and the like, powders such as pancake mix, flour, rice cake and the like, noodles such as buckwheat noodle, wheat noodle and the like, and so on.

By adding a predetermined amount of TGF-β to diets containing causal substances of food allergies beforehand by mixing, blending or the like, when the diet containing the causal substance of the food allergy is taken erroneously, it is possible to prevent a crisis of allergic symptoms. Particularly, this method is effective on an anaphylactic shock symptom and the like that are lethal allergic symptoms caused by intake.

The predetermined amount is set in consideration of types of diets, intake per day, age of an administration target body and like, and it is preferable that a total intake of TGF-β per day is set at 100 µg/kg or more relative to a weight of an administration target body. Particularly, in terms of safety, it is preferable that a total intake of TGF-β per day is set at a range of 100 µg/kg to 200 µg/kg relative to a weight of an administration target body.

As in the allergy prevention method or treatment method, a maximum intake of TGF-β of an infant per day is 200 µg/kg, and therefore, it is estimated that a total intake of maximum 200 µg/kg per day relative to a weight of a target body can be taken safely as a diet.

The invention is of an oral drug selected from a group consisting of allergy preventive drugs, allergy treatment drugs, immune activation drugs, antitumor drugs, antiinfectants, and antiviral drugs characterized by selectively suppressing Th2 immune response by containing transforming growth factor-beta (TGF-β) in a range of 100 µg/day to 100 µg/day in administration. Further, the invention is of an oral drug characterized by suppressing Th2 immune response while maintaining or enhancing Th1 immune response by oral administration of the TGF-β. Furthermore, the invention is of an oral drug characterized by enhancing Th1 immune response by oral administration of the TGF-β.

Among forms of the oral drug are pill, granule, capsule, suspension and the like.

The predetermined amount is set in consideration of an age and weight of an administration target body, symptoms and diseases targeted for prevention and/or treatment and like, and it is preferable that an intake of TGF-β per day or per dose is set at 100 µg/kg or more relative to a weight of an administration target body. An intake of TGF-β per day or per dose is preferably set at a range of 100 µg/kg to 500 µg/kg relative to a weight of an administration target body, and more preferably, at a range of 100 µg/kg to 200 µg/kg relative to the weight, particularly, in terms of safety.

As in the allergy prevention method or treatment method, a maximum intake of TGF-β of an infant per day is 200 µg/kg, and therefore, it is estimated that an intake of maximum 200 µg/kg per day or per dose relative to a weight of an administration target body can orally be administered safely as an oral drug.

From previous experiments, an administration amount per day or per dose of TGF-β verified to have prevention and treatment effects ranges from 100 µg/kg to 500 µg/kg relative to a weight of an administration target body, and application to oral drugs are expected as prevention/treatment drugs of various diseases. However, as described above, since an administration amount for the human estimated to be safe is up to 200 µg/kg relative to a weight of an administration target body, thorough clinical studies on adverse reaction and the like are considered necessary for oral administration of TGF-β ranging from 200 µg/kg to 500 µg/kg or exceeding 500 µg/kg relative to a weight of an administration target body.

Embodiments of the invention will be described below based on Examples, but the invention is not limited to these Embodiments.

Embodiment 1

Prevention of Symptoms of a Food Allergy by Administered High-dose TGF-β

<Suppression of Production of IgE Antibody>

Using ovalbumin (OVA) specific T cell receptor (TCR) transgenic mice (DO11.11 mice), verified was the effect of preventing allergic symptoms of orally administered TGF-β.

The transgenic mice (DO11.10 mice) are of a model mouse for food allergy such that repeated OVA oral administration induces OVA-specific IgE (immune globulin E) production in blood and an anaphylactic shock after an intravenous injection of OVA (Shida et al., J Allergy Clin Immunol vol. 105: 788, 2000).

The food allergy model mice (DO11.10, 6-8 weeks old, weight of 20 to 30 grams) were fed with 100 mg OVA (SIGMA™ Chemical Inc.) plus control vehicle or with 100 mg OVA and 5 µg TGF-β (R&D SYSTEMS™ Inc.) every other day repeatedly for a total of six times. Two days (nine days) after the last feeding, serums of total three mice including model mice of respective cases and a model mouse without feeding of OVA as a control were taken, and production amounts of IgE antibody were measured by ELISA (Enzyme Linked Immuosorbent assay).

As shown in. FIG. 1A, IgE antibody remarkably increased in the model mouse fed with OVA plus vehicle, while IgE antibody was not detected in the serum of the model mouse fed with TGF-β simultaneously with OVA. It is thus considered that TGF-β orally administered simultaneously with OVA provoking the allergy suppressed production of IgE antibody. Further, this result was the same as in nine days after the last feeding, and therefore, suppression of production of IgE antibody by TGF-β is not considered transient.

Figure 1B:
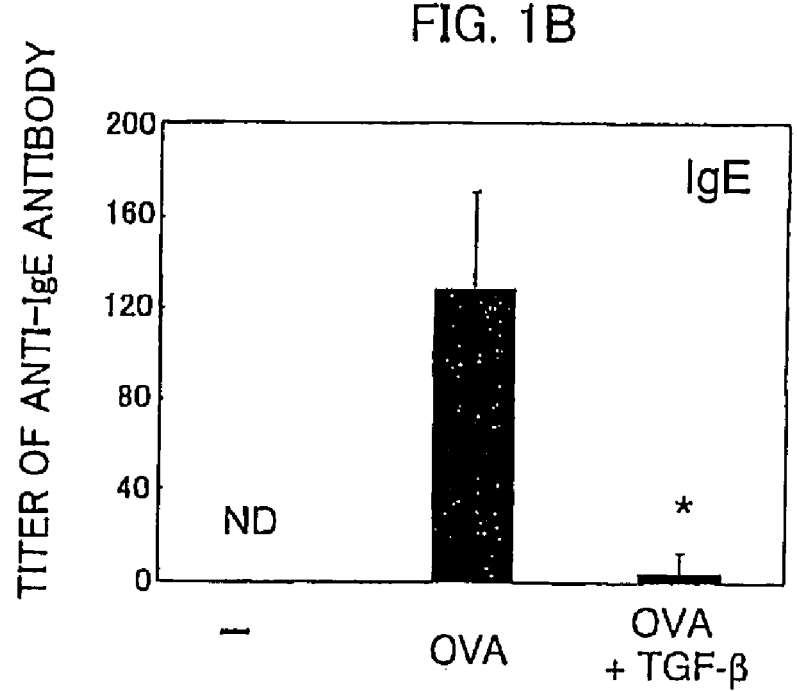
FIG. 1B is a graph illustrating suppression of production of serum IgE antibody by orally administered TGF-β of Embodiment 1.

FIG. 1B shows a result of measuring the amount of production of OVA specific IgE antibody in the serum using PCA (Passive Cutaneous Anaphylaxis). As in the result of ELISA of FIG. 1A, it is understood that TGF-β suppressed production of OVA specific IgE antibody.

<Suppression of Production of Molecule Involved in Immune Response>

Figure 2:
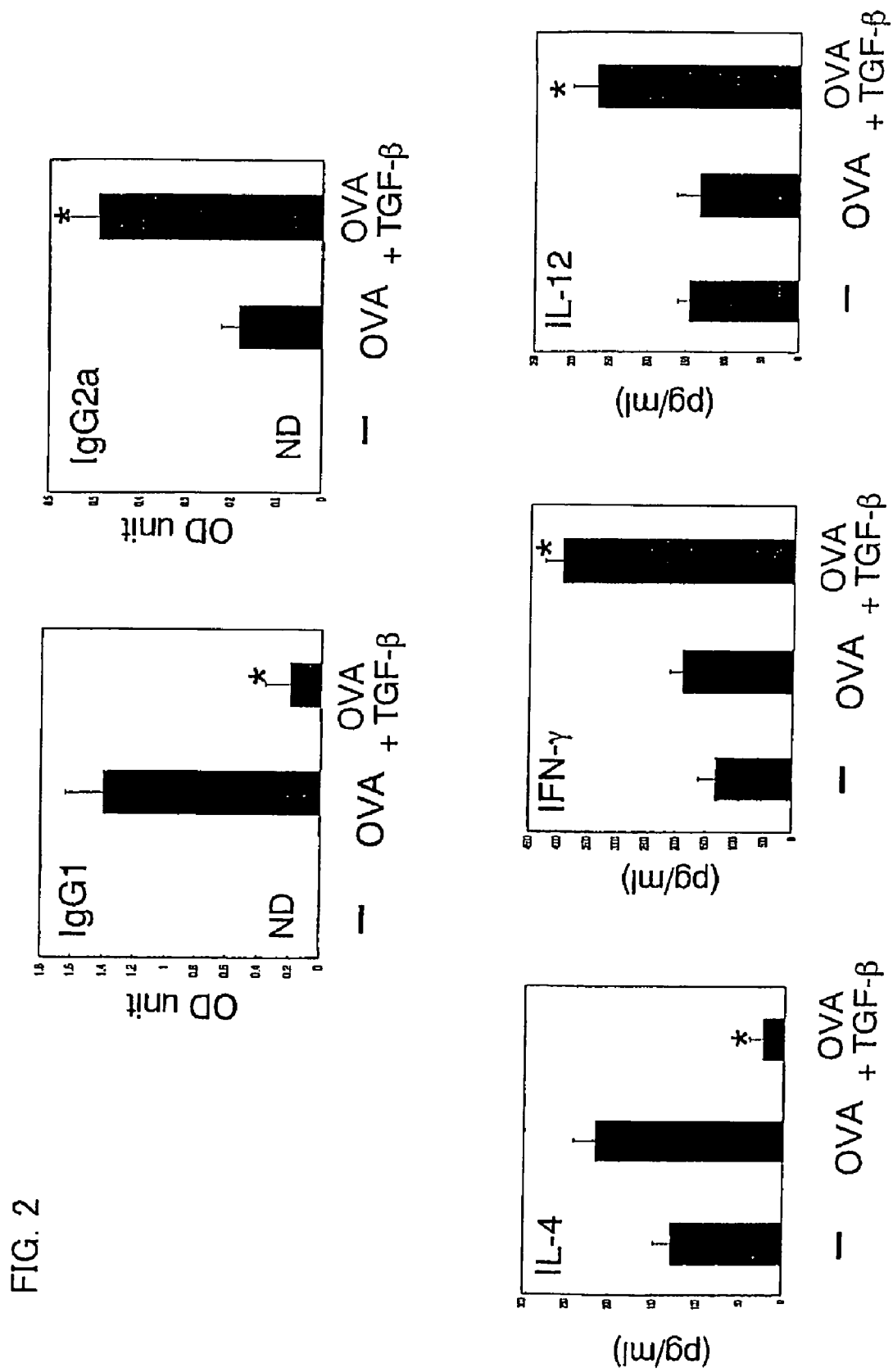
FIG. 2 is a graph illustrating effects of orally administered TGF-β on production of bioactive molecules (IgG antibody, IL-4, IL-12 and IFN-γ)

FIG. 2 shows results of measurements of concentrations in serum and production amounts in spleen cells of mice with respect to five molecules involved in immune response except IgE antibody (OVA-specific IgG antibody and cytokines): IgG1 (immunoglobulin G1), IgG2a (immunoglobulin Ga), IL-4 (inteleukin-4), IFN-γ (interferon-γ) and IL-12 (inteleukin-12).

Amounts of OVA-specific IgG1 antibody and IgG2a antibody in serums of model mice were assessed in optical density (OD unit) by ELISA, and results were obtained that simultaneous administration of TGF-β suppressed production of IgG1 antibody considered involved in Th2 immune response (allergic reaction and the like) as in IgE (upper left in FIG. 2), while increasing, rather than suppressing, the production amount by more than two times of IgG2a antibody considered involved in Th1 immune response (protective immunity against the cancer and injection and the like) (upper right in FIG. 2), Further, the result was obtained that administration of TGF-β suppressed the amount of production in mouse spleen cell of IL-4 that specifically produces IgE antibody, while enhancing amounts of production in mouse spleen cell of interferon γ (IFN-γ) considered involved in antivirus action, immune enhancement action and antitumor action and of IL-12 considered activating NK cells and cell immunity, as in IgG2a antibody (lower stage in FIG. 2).

From the results as described above, it was clarified that high-dose administration of TGF-β selectively suppresses production of bioactive molecules involved in Th2 immune response, while enhancing production of bioactive molecules involved in Th1 immune response.

<Effect of Anti-TGF-β Antibody>

The food allergy model mice (DO11.10, 6-8 weeks old, weight of 20 to 30 grams) were given feeding with 100 mg OVA plus control vehicle, subcutaneous injection of 100 mg OVA, 5 µg TGF-β and IgG antibody (control antibody), or subcutaneous injection of 100 mg OVA, 5 µg TGF-β and anti-TGF-β antibody (<TGF-® Ab) every other day repeatedly for a total of six times. Two days (nine days) after the last feeding, serums of total three mice including respective model mice were taken, and production amounts of IgE antibody were measured by ELISA and PCA, while production amounts of IgG2a antibody were measured by ELISA. The results are shown in FIGS. 3A and 3B.

Figure 3A:
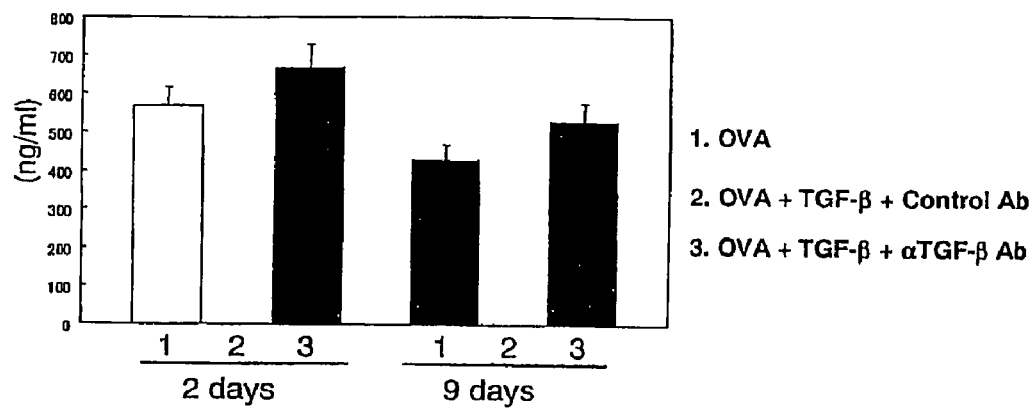
FIG. 3A is a graph illustrating effects of intravenously administered anti-TGF-β antibody on the immune system by orally administered TGF-β.
Figure 3B:
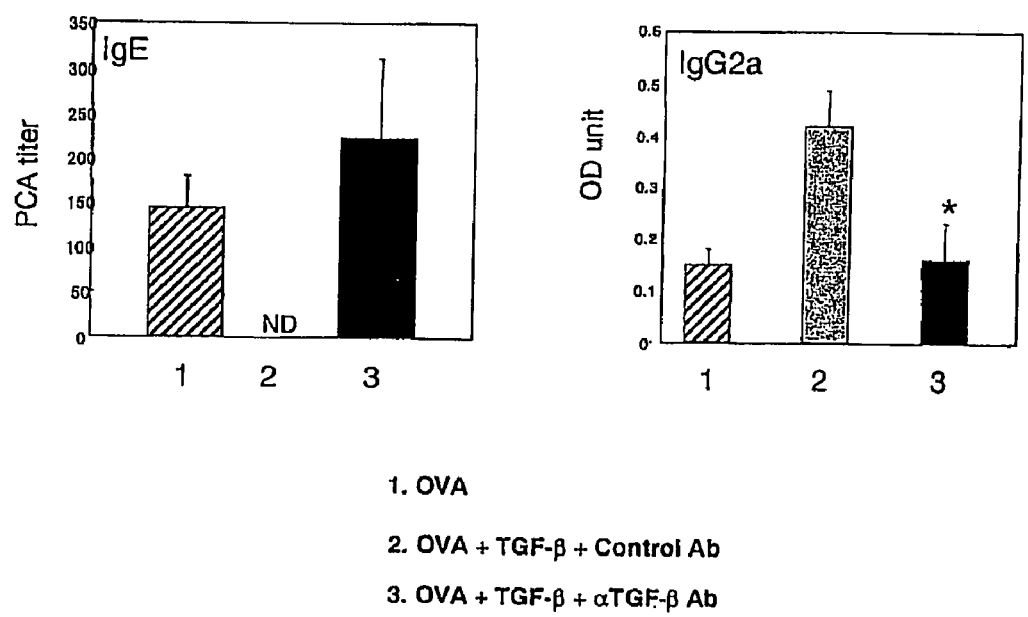
FIG. 3B is a graph illustrating effects of intravenously administered anti-TGF-β antibody on the immune system by orally administered TGF-β.

As shown in FIGS. 3A and 3B, it is understood that anti-TGF-β antibody administered by subcutaneous injection inhibited both the suppression of production of IgE antibody and the enhancement of production of IgG2 antibody by orally administered TGF-β. From the results, it is confirmed that TGF-β orally administered and absorbed/metabolized from gastrointestine suppresses Th2 immune response involving IgE antibody, while enhancing Th1 immune response involving IgG2 .

From the results as described above, it is considered that orally administered TGF-β is not decomposed in gastrointestine, and metabolized in a different pathway from that of transdermally/intravenously administered TGF-β to modify immune response.

<Suppression of Anaphylactic Shock>

The allergic disease model mice (DO11.10, 6-8 weeks old, weight of 20 to 30 grams) were given feeding or injection with 100 mg OVA plus control vehicle, 100 mg OVA and 5 µg TGF-β, or 5 µg TGF-β every other day for a total of six times. Two days after the last feeding, OVA was intravenously injected, and Table 1 shows results of observation on whether or not an anaphylactic shock was developed.

TABLE 1

| Mice | No. of the mice showing anaphylactic reaction | | | |
|---|---|---|---|---|
| | − | + | ++ | +++ |
| control | 4 | 0 | 0 | 0 |
| OVA | 0 | 1 | 4 | 1 |
| OVA + TGF-β1 | 4 | 2 | 0 | 0 |
| TGF-β1 | 4 | 0 | 0 | 0 |

Six model mice were examined on each of conditions of 100 mg OVA plus control vehicle, and 100 mg OVA and 5 µg TGF-β, and four model mice were examined on each of conditions of control (without feeding) and 5 µg TGF-µ.

Almost all of the mice fed with only OVA developed fetal anaphylactic shocks of level "++" to "+++". In contrast thereto, it was clarified that the model mice fed with orally administered TGF-β were suppressed to an almost no shock state of level "−" to "+".

From the results, it was clarified that the anaphylactic shock that is a severe allergic symptom can be suppressed by orally administering high-dose TGF-β simultaneously with an allergy causal substance.

<Comparison with Transdermal/Intravenous Administration>

Figure 4A:
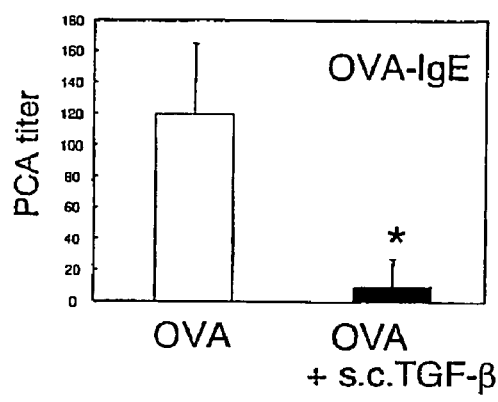
FIG. 4A is a graph illustrating suppression of production of serum IgE antibody by intravenously administered TGF-β.
Figure 4B:
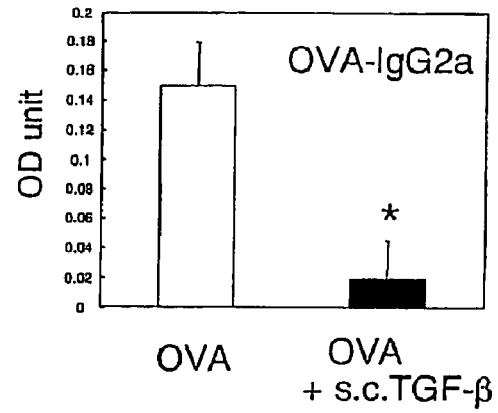
FIG. 4B is a graph illustrating suppression of production of serum IgG2 antibody by intravenously administered TGF-β.

As comparative experiments with conventional transdermal/intravenous administration, the allergic disease model mice (DO11.10, 6-8 weeks old, weight of 20 to 30 grams) were given feeding and a subcutaneous injection of 100 mg OVA and 5 µg TGF-β every other day for a total of six times. Two days after the last feeding, amounts of production of serum IgE antibody were measured by PCA, and amounts of production of serum IgG2a antibody were measured by ELISA. The results are shown in FIGS. 4A and 4B.

Administration of TGF-β suppressed production of serum IgE antibody as in oral administration, but also suppressed production of serum IgG2a antibody that was enhanced in oral administration. In other words, transdermal administration of TGF-β suppresses both the allergic reaction (Th2 immune response) and protective immunity (Th1 immune response) against the infection and cancer. A risk of immune deficiency thereby arises.

Meanwhile, oral administration of TGF-β is capable of suppressing only the allergic reaction (Th2 immune response) without degrading the immune response capability (suppressing Th1 immune response) necessary to maintain life. It is thus possible to prevent and/or treat the allergic disease without trouble such as adverse reaction, immune deficiency and the like developing in transdermally/intravenously administering TGF-β.

Further, orally administered TGF-β enhances Th1 immune response involved in cell immunity, and therefore, is considered effective in preventing and/or treating allergic symptoms, various diseases such as cancers and infections and the like.

Embodiment 2

Treatment of Allergic Symptoms

<Treatment of Atopic Dermatitis>

Figure 5A:
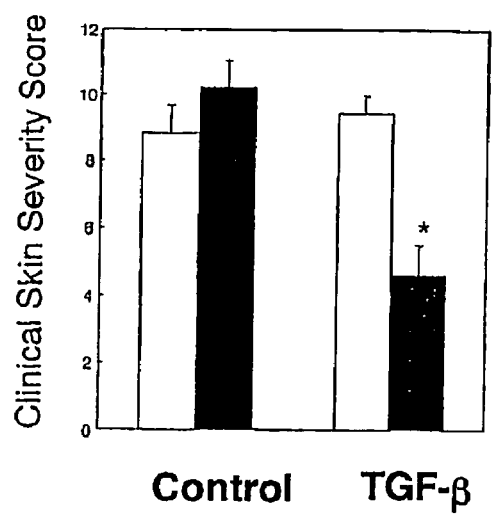
FIG. 5A is a graph illustrating a treatment effect on allergic symptom (eczema) by orally administered TGF-β of Embodiment 2.
Figure 5B:
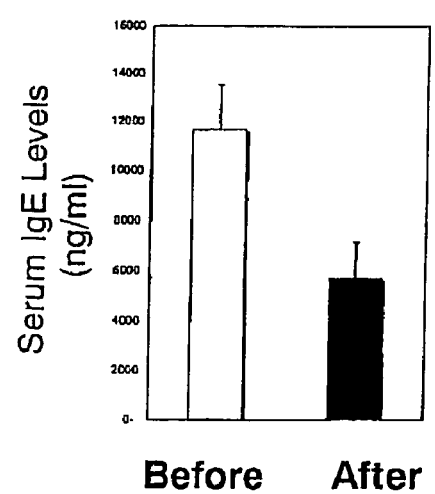
FIG. 5B is a graph illustrating suppression of production of IgE antibody by orally administered TGF-β of Embodiment 2.

Each of model mice (DO11.10, 6-8 weeks old, weight of 20 to 30 grams) actually developing atopic dermatitis was fed with oral administration of 5 µg TGF-β per dose every other day for a total of three times. FIGS. 5A and 5B show clinical skin severity and IgE level in serum before and one week after oral TGF-β administration, respectively.

It was clarified that orally TGF-β administered model mice developed alleviated inflammation of atopic dermatitis (FIG. 5A) and decreased IgE level (FIG. 5B) as compared with before administration. The model mice did not develop symptoms such as adverse reaction and the like by orally administered TGF-β.

It is thus possible to treat and alleviate already developed allergic symptoms by orally administering high-dose TGF-β.

This application is based on the Japanese Patent application No. 2005-252912 filed on Aug. 31, 2005, entire content of which is expressly incorporated by reference herein.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method of treating a food allergy, wherein said method comprises:
   providing isolated transforming growth factor beta 1 (TGF-β1) in an amount of 100 µg/kg to 250 µg/kg, relative to a weight of an administration target body,
   providing a causal substance of allergy,
   combining the isolated TGF-β1 and causal substance of allergy,
   administering orally and simultaneously the combination to the administration target body in need thereof,
   wherein said causal substance of allergy is at least one food allergen and,
   wherein the method of treating allergy results in a non-transient immunological response;
   thereby treating the food allergy.

2. The allergy treatment method according to claim 1, wherein the TGF-β1 is human TGF-β1.

3. The method according to claim 1, wherein said administration target body is a human.

4. The method according to claim 1, wherein said administration target body is a mouse.

5. The method according to claim 1, wherein the combination is administered every other day for a total of six dosages.

6. The method of treating allergy according to claim 1, wherein 5 µg of TGF-β1 are administered simultaneously with oral intake of the causal substance of allergy, to a mouse.

7. The method according to claim 1, wherein the causal substance of allergy is administered to the target body in an amount of from 3 to 5 mg per gram of target body weight.

8. The method of claim 1, wherein the food allergen is selected from the group consisting of milk, egg, rice, buckwheat, seafood and mixtures thereof.

9. The method of claim 1, wherein the causal substance of allergy is ovalbumin of an egg.

10. The method of claim 1, wherein the food allergen is in a milk product.

11. The method of claim 1, wherein the food allergen is in a rice cake.

12. The method of claim 1, wherein the food allergen is in a yogurt.

13. The method of claim 1, wherein the food allergen is in a noodle.

14. The method of claim 1, wherein the food allergen is in a flour.

15. The method of claim 1, wherein the food allergen is in a pancake mix.

16. The method of claim 1, wherein the food allergen is in a chocolate.

17. The method of claim 1, wherein the food allergen is in a biscuit.

18. The method of claim 1, wherein the food allergen is in a pudding.

* * * * *